United States Patent
Lee et al.

(10) Patent No.: US 11,045,785 B2
(45) Date of Patent: Jun. 29, 2021

(54) METAL-ORGANIC FRAMEWORK, METHOD FOR PREPARING THE SAME, AND ADSORPTION DEVICE EMPLOYING THE SAME

(71) Applicant: Industrial Technology Research Institute, Hsinchu (TW)

(72) Inventors: Wei-Chih Lee, Kaohsiung (TW); Chang-Yi Shen, Zhubei (TW); Jiun-Jen Chen, New Taipei (TW); Yuhao Kang, Zhubei (TW); Shih-Yun Yen, New Taipei (TW); Yu-Xuan Wang, New Taipei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 16/672,941

(22) Filed: Nov. 4, 2019

(65) Prior Publication Data
US 2020/0139343 A1    May 7, 2020

Related U.S. Application Data (63) Continuation-in-part of application No. 16/214,600, filed on Dec. 10, 2018.

(30) Foreign Application Priority Data

Nov. 5, 2018 (TW) .................................. 107139167
Jul. 18, 2019 (TW) .................................. 108125394

(51) Int. Cl.
*B01D 53/02* (2006.01)
*B01J 20/22* (2006.01)
(Continued)

(52) U.S. Cl.
CPC ............ *B01J 20/226* (2013.01); *B01D 53/02* (2013.01); *B01J 20/28066* (2013.01);
(Continued)

(58) Field of Classification Search
CPC ...... B01D 53/02; B01D 53/04; B01D 53/261; B01D 2253/204; B01D 2257/80;
(Continued)

(56) References Cited

U.S. PATENT DOCUMENTS 8,133,301 B2    3/2012    Hwang et al.
8,283,468 B2 *  10/2012   Sakai ................... C07F 1/005
                                                      546/5
(Continued)

FOREIGN PATENT DOCUMENTS

CN    102962036 A    3/2013
CN    107722290 A    2/2018
(Continued)

OTHER PUBLICATIONS

Burtch et al., "Water Stability and Adsorption in Metal-Organic Frameworks," Chemical Reviews, vol. 114, Sep. 29, 2014, pp. 10575-10612.
(Continued)

*Primary Examiner* — Frank M Lawrence, Jr.
(74) *Attorney, Agent, or Firm* — Birch, Stewart, Kolasch & Birch, LLP (57) ABSTRACT

A metal organic framework and a method for preparing the same, and an adsorption device employing the metal organic framework are provided. The metal organic framework includes a 3,5-pyridinedicarboxylic acid and a metal ion, which is an aluminum ion, a chromium ion, or a zirconium ion, wherein the 3,5-pyridinedicarboxylic acid is coordinated to the metal ion.

12 Claims, 4 Drawing Sheets

(51) Int. Cl.
  *B01J 20/30* (2006.01)
  *B01J 20/28* (2006.01)
  *C07C 51/41* (2006.01)

(52) U.S. Cl.
  CPC ......... *B01J 20/3078* (2013.01); *C07C 51/418* (2013.01); *B01D 2253/204* (2013.01); *B01D 2257/80* (2013.01)

(58) Field of Classification Search
  CPC ............... B01J 20/226; B01J 20/28066; B01J 20/28016; B01J 20/3078; C07C 51/418; C07D 213/80; C07F 11/005; C07F 5/069; C07F 7/003
  USPC .................................... 96/108, 154; 502/401
  See application file for complete search history.

(56) References Cited

U.S. PATENT DOCUMENTS

| | | | |
|---|---|---|---|
| 8,524,932 B2 | 9/2013 | Leung et al. | |
| 8,734,652 B2 | 5/2014 | Kiener et al. | |
| 8,980,128 B2 | 3/2015 | Chang et al. | |
| 9,102,691 B2 | 8/2015 | Zhou et al. | |
| 9,724,668 B2 | 8/2017 | Zhou et al. | |
| 9,758,532 B2 | 9/2017 | Dinca et al. | |
| 10,702,851 B2* | 7/2020 | Ohashi | C07F 7/003 |
| 2006/0287190 A1* | 12/2006 | Eddaoudi | B01J 31/2239 502/60 |
| 2008/0306315 A1 | 12/2008 | Lillerud et al. | |
| 2014/0212944 A1* | 7/2014 | Tian | B01J 31/1691 435/180 |
| 2015/0291870 A1 | 10/2015 | Van Horn et al. | |
| 2017/0166661 A1* | 6/2017 | Liang | A61K 47/6949 |
| 2017/0341010 A1 | 11/2017 | Dinca et al. | |
| 2018/0133684 A1* | 5/2018 | Chang | B01D 53/04 |
| 2019/0022622 A1* | 1/2019 | Park | B01J 20/2808 |
| 2019/0194232 A1* | 6/2019 | Ohashi | B01J 20/226 |
| 2020/0054991 A1* | 2/2020 | Humphrey | B01J 20/28064 |

FOREIGN PATENT DOCUMENTS

| | | |
|---|---|---|
| EP | 2502671 A2 | 9/2012 |
| TW | 200744703 A | 12/2007 |

OTHER PUBLICATIONS

Canivet et al., "Water adsorption in MOFs: fundamentals and applications," Chem Soc Rev, vol. 43, May 29, 2014, 24 pages.

Taiwanese Office Action and Search Report, dated Mar. 14, 2019, for Taiwanese Application No. 107139167.

Taiwanese Office Action and Search Report, dated Apr. 7, 2020, for Taiwanese Application No. 108125394.

* cited by examiner

METAL-ORGANIC FRAMEWORK, METHOD FOR PREPARING THE SAME, AND ADSORPTION DEVICE EMPLOYING THE SAME

CROSS REFERENCE TO RELATED APPLICATIONS

This application is a Continuation-In-Part of pending U.S. patent application Ser. No. 16/214,600, filed Dec. 10, 2018 and entitled "Metal-organic framework, method for preparing the same, and adsorption device employing the same", the entirety of which is incorporated by reference herein, which claims priority from, Taiwan Application Ser. No. 107139167, filed on Nov. 5, 2018, the disclosure of which is hereby incorporated by reference herein in its entirety.

This application is based upon and claims the benefit of priority from the prior Taiwan Patent Application No. 108125394, filed on Jul. 18, 2019, the entire contents of which are incorporated herein by reference.

TECHNICAL FIELD

The disclosure relates to a metal-organic framework and a method for preparing the same, and in particular to a metal-organic framework with a great water adsorption amount under a low relative humidity.

BACKGROUND

Moisture-adsorbent materials are widely used in the adsorption dryers of compressed-air systems. After passing through an air compressor, the introduced ambient air has a relative humidity above 80%. Thus, most of the moisture content of the introduced ambient air must be removed by a freeze dryer, and then the remaining moisture content of the introduced ambient air is removed by an adsorption dryer. After being treated with the freezer dryer, the introduced ambient air has a relative humidity less than 30%. The compressed air is then treated with the adsorption dryer to remove the remaining moisture content. Therefore, the moisture-adsorbent materials employed by the adsorption dryer should exhibit a high water adsorption amount under extremely low relative humidity, thereby lessening the equipment size, reducing the construction cost, and improving the operational efficiency.

Conventional moisture-adsorbent materials like zeolite 4A exhibit a good water adsorption amount under low relative humidity. The high hydrophilicity of zeolite 4A increases the difficulty of moisture desorption. In general, the moisture adsorbed by zeolite 4A would be desorbed therefrom at a temperature of about 140° C.-160° C. or more. However, moisture desorption performed at high temperatures will not only cause a large amount of energy to be consumed as a result of the regeneration of moisture-adsorbent materials, but also increases inconvenience during use. In view of this, there has been an increasing demand for moisture-adsorbent materials that can adsorb moisture at a low relative humidity and desorb moisture at low temperatures.

Conventional moisture-adsorbent materials, however, exhibit low water adsorption amounts at a low relative humidity. Furthermore, moisture adsorbed by conventional moisture-adsorbent materials would be desorbed therefrom at a temperature above 140° C. As a result, the energy consumption and operating cost of the device employing the conventional moisture-adsorbent materials are increased.

Accordingly, a novel metal-organic framework is required to solve the aforementioned problems.

SUMMARY

According to embodiments of the disclosure, the disclosure provides a metal-organic framework. The metal-organic framework includes a 3,5-pyridinedicarboxylic acid and a metal ion, wherein the 3,5-pyridinedicarboxylic acid is coordinated to the metal ion. In particular, the metal ion is an aluminum ion, a chromium ion, or a zirconium ion.

According to another embodiment of the disclosure, the disclosure provides a method for preparing the metal-organic framework. The method for preparing the metal-organic framework includes providing a composition, wherein the composition includes a 3,5-pyridinedicarboxylic acid, a metal compound, and a solvent. Next, the composition is subjected to a heating process, so that the 3,5-pyridinedicarboxylic acid reacts with the metal compound, obtaining a metal-organic framework. According to another embodiment of the disclosure, the solvent includes an organic solvent, water, or a combination thereof.

According to another embodiment of the disclosure, the disclosure also provides an adsorption device. The adsorption device includes a carrier and an adsorption material. In particular, the adsorption material is disposed on the carrier. The adsorption material can be the aforementioned metal-organic framework.

A detailed description is given in the following embodiments with reference to the accompanying drawings.

DETAILED DESCRIPTION

In the following detailed description, for the purposes of explanation, numerous specific details are set forth in order to provide a thorough understanding of the disclosed embodiments. It will be apparent, however, that one or more embodiments may be practiced without these specific details. In other instances, well-known structures and devices are shown schematically in order to simplify the drawing.

Embodiments of the disclosure provide a metal-organic framework, a method for preparing the same, and an adsorption device employing the metal-organic framework. The metal-organic framework of the disclosure exhibits a rapid water adsorption property under a low relative humidity.

Herein, the term "low relative humidity" refers to the atmosphere having a relative humidity of 30% and the atmosphere having a temperature of 25° C. The metal-organic framework can be further disposed on a carrier to obtain an adsorption device. The adsorption device can be used in an adsorption dryer to achieve the desired rapid water adsorption property under a low relative humidity.

According to embodiments of the disclosure, the disclosure provides a metal-organic framework. The metal-organic framework includes a 3,5-pyridinedicarboxylic acid and a metal ion, wherein the 3,5-pyridinedicarboxylic acid is coordinated to the metal ion. In particular, the metal ion is an aluminum ion, a chromium ion, or a zirconium ion. The molar ratio of 3,5-pyridinedicarboxylic acid to the metal ion is from 3:1 to 1:2. When the molar ratio of 3,5-pyridinedicarboxylic acid to the metal ion is less than 1:2, the metal-organic framework exhibits a low water adsorption amount since the metal-organic framework would not be a porous material. When the molar ratio of 3,5-pyridinedicarboxylic acid to the metal ion is greater than 3:1, the metal-organic framework also exhibits a low water adsorption amount since the metal-organic framework would not be a porous material.

According to embodiments of the disclosure, the disclosure provides a method for preparing the aforementioned metal-organic framework. First, a composition is provided, wherein the composition includes a 3,5-pyridinedicarboxylic acid, a metal compound, and a solvent. Next, after uniformly mixing the composition, the composition is subjected to a heating process so that the 3,5-pyridinedicarboxylic acid reacts with the metal compound, obtaining a metal-organic framework.

According to embodiments of the disclosure, the molar ratio of 3,5-pyridinedicarboxylic acid to the metal compound is from 3:1 to 1:2, such as 2:1 or 1:1.

According to embodiments of the disclosure, the metal compound can be aluminum salt, chromium salt, zirconium salt, or a combination thereof. In particular, the metal compound can be aluminum nitrate, aluminum sulfate, aluminum chloride, aluminum phosphate, chromium nitrate, chromium phosphate, zirconium nitrate, zirconium phosphate, zirconyl chloride, or a combination thereof.

According to embodiments of the disclosure, the metal compound in the composition has an initial concentration from 0.15 mol/L to 0.66 mol/L, based on the volume of the solvent.

According to embodiments of the disclosure, the heating process can have a temperature from about 100° C. to 150° C., such as from 110° C. to 140° C. In addition, the heating process can be performed for a period of 1 hr to 66 hrs.

According to another embodiment of the disclosure, the solvent includes an organic solvent, water, or a combination thereof. According to another embodiment of the disclosure, the solvent is an organic solvent. According to another embodiment of the disclosure, the solvent is water. According to another embodiment of the disclosure, the solvent may consist of an organic and water, wherein the weight ratio of the organic solvent to water may be between 1:99 and 99:1 (such as between 1:99 and 1:29, between 1:99 and 1:1, between 10:90 and 2:1, or between 1:1 and 99:1). For example, the weight ratio of the organic solvent to water may be 4:1, 2:1, 1:1, 1:2, 1:4, or 1:8. The organic solvent of the disclosure may be N,N-dimethylformamide, N,N-diethylformamide, N,N-dimethylacetamide, or a combination thereof. According to another embodiment of the disclosure, the solvent is water, N,N-dimethylformamide, N,N-diethylformamide, N,N-dimethylacetamide, or a combination thereof.

According to embodiments of the disclosure, the composition may consist of 3,5-pyridinedicarboxylic acid, metal compound, and organic solvent. When the composition consists of 3,5-pyridinedicarboxylic acid, metal compound, and organic solvent, the heating process can have a temperature from about 100° C. to 150° C., such as from 120° C. to 140° C. In addition, the heating process can be performed for a period of 12 hrs to 66 hrs, such as 12 hrs to 48 hrs, or 24 hrs to 48 hrs. An initial concentration of the metal compound in the composition may be between 0.15 mol/L and 0.33 mol/L, based on the volume of the solvent.

According to embodiments of the disclosure, when the solvent is water, the composition further includes an alkali metal hydroxide. Namely, the composition may consist of 3,5-pyridinedicarboxylic acid, metal compound, water, and alkali metal hydroxide. The alkali metal hydroxide may include lithium hydroxide, sodium hydroxide, potassium hydroxide, or a combination thereof.

According to embodiments of the disclosure, when the solvent is water, the composition further includes an alkali metal hydroxide and aluminate. Namely, the composition may consist of 3,5-pyridinedicarboxylic acid, metal compound, water, alkali metal hydroxide, and aluminate. The aluminate includes lithium aluminate, sodium aluminate, potassium aluminate, magnesium aluminate, calcium aluminate, or a combination thereof. Furthermore, an initial concentration of the aluminate in the composition is between 0.05 mol/L and 0.20 mol/L (such as between 0.05 mol/L and 0.15 mol/L), based on the volume of the water.

According to embodiments of the disclosure, the composition does not include alcohol (i.e. the composition is in the absence of alcohol (such as ethanol)). According to one embodiment of the disclosure, when the solvent is water, the composition does not include alcohol.

According to embodiments of the disclosure, when the solvent is water, the addition of alkali metal hydroxide can neutralize the 3,5-pyridinedicarboxylic acid in the composition, in order to keep the composition (i.e. an aqueous solution) at neutral pH (i.e. the composition has a pH between 6 and 8), obtaining a composition which is able to be dissolved in water. Accordingly, the molar ratio of the alkali metal hydroxide to 3,5-pyridinedicarboxylic acid may be between 1.8 and 2.2, such as 2. Therefore, if the molar ratio of the alkali metal hydroxide to 3,5-pyridinedicarboxylic acid is too low or too large, alkali metal hydroxide cannot completely neutralize the 3,5-pyridinedicarboxylic acid in the composition, resulting in that the obtained metal-organic framework exhibits a low water adsorption amount or there is even no metal-organic framework obtained.

According to embodiments of the disclosure, when the solvent is water, the addition of the aluminate can inhibit the formation of crystalline by-products when reacting 3,5-pyridinedicarboxylic acid with the metal compound, thereby preventing the water adsorption amount of the metal-organic framework from being reduced by the crystalline by-products.

According to embodiments of the disclosure, when the solvent is water, the waste effluent, which is obtained after reacting the 3,5-pyridinedicarboxylic acid with the metal compound, does not contain any organic solvent. As a result, the cost for treating waste effluent can be reduced and the pollution problems caused by the waste effluent can be mitigated. When the composition consists of 3,5-pyridinedicarboxylic acid, metal compound, water, alkali metal hydroxide, and aluminate, the heating process can have a temperature from about 100° C. to 150° C., such as from 110° C. to 130° C. In addition, the heating process can be performed for a period of 2 hr to 3 hrs. The initial concentration of the metal compound in the composition may be between 0.15 mol/L and 0.66 mol/L, based on the volume of water. As a result, when the solvent is water, the time period for fabricating the metal-organic framework can be reduced, thereby increasing the yield of the metal-organic framework.

According to embodiments of the disclosure, when the solvent consists of water and organic solvent and the weight ratio of the organic to water is between 1:29 and 1:99, the composition further includes an alkali metal hydroxide and an aluminate. According to embodiments of the disclosure, when the weight ratio of the organic to water is between 1:29 and 1:99, the obtained metal-organic framework exhibits low water adsorption amount or there is even no metal-organic framework obtained.

Furthermore, an initial concentration of the aluminate in the composition is between 0.05 mol/L and 0.20 mol/L (such as between 0.05 mol/L and 0.15 mol/L), based on the volume of the solvent.

Figure 6:
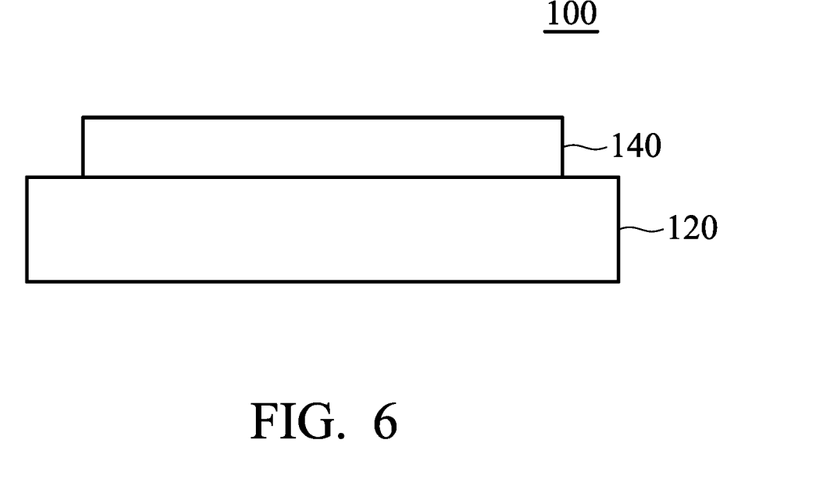
FIG. 6 is a schematic view of an adsorption device according to an embodiment of the disclosure.

According to embodiments of the disclosure, as shown in FIG. 6, the disclosure provides an adsorption device 100. The adsorption device 100 includes a carrier 120 and an adsorption material 140. The adsorption material can be disposed on the carrier. The adsorption material can include a 3,5-pyridinedicarboxylic acid and a metal ion, wherein the 3,5-pyridinedicarboxylic acid is coordinated to the metal ion. In particular, the metal ion is an aluminum ion, a chromium ion, or a zirconium ion. According to embodiments of the disclosure, the adsorption material exhibits a water adsorption amount from 18 wt % to 40 wt % after disposing the adsorption device under a relative humidity of 30% at 25° C. for 30 minutes.

Herein, the water adsorption amount in the disclosure is determined using the following equation:

$$\text{water absorption amount} = \frac{W_1 - W_0}{W_0} \times 100\%,$$

wherein $W_1$ refers to the weight of the adsorption material after water adsorption, and $W_0$ refers to the weight of the adsorption material after water desorption at 80° C.

According to embodiments of the disclosure, the adsorption material can be used under a low relative humidity. Furthermore, the adsorption material can be used in an adsorption dryer such as high-pressure air dryer or plastic dryer. Moreover, the adsorption material can serve as an adsorbent for removing specific harmful small-molecule compound or gas.

Below, exemplary embodiments will be described in detail with reference to the accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

EXAMPLES

Preparation of Metal-Organic Framework

Preparation Example 1

First, aluminum nitrate (Al(NO$_3$)$_3$.9H$_2$O) (0.015 mol), 3,5-pyridinedicarboxylic acid (0.015 mol), water (72 mL) and dimethylformamide (18 mL) were mixed, wherein the molar ratio of the 3,5-pyridinedicarboxylic acid to the aluminum nitrate was 1:1. Next, the mixture was stirred at 120° C. for 48 hrs. Next, after cooling to room temperature, yellow sediment was collected. After washing the yellow sediment with water and filtering, a yellow solid was obtained. Next, the yellow solid was dried with a dryer (having a drying temperature of about 140° C.) overnight. After drying, the yellow solid was ground into powder. Next, the powder was subjected to a vacuum drying process in a vacuum drying oven, wherein the temperature of the vacuum drying process was about 140° C., and the vacuum drying process was performed for a period of 6 hrs. After cooling to room temperature, a metal-organic framework (yellowish powder) (1) was obtained. The characteristics of the metal-organic framework (1) were determined by a specific surface area and porosimetry analyzer. The metal-organic framework (1) had a specific surface area of 1133 m$^2$/g and a water adsorption amount of 34.48 wt %. The water adsorption amount was determined using the following equation:

$$\text{water absorption amount} = \frac{W_1 - W_0}{W_0} \times 100\%,$$

wherein $W_1$ was the weight of the adsorption material after water adsorption, and $W_0$ was the weight of the adsorption material after water desorption at 80° C.

Preparation Example 2

Preparation Example 2 was performed in the same manner as Preparation Example 1 except that the molar ratio of the 3,5-pyridinedicarboxylic acid to the aluminum nitrate was increased from 1:1 to 2:1, obtaining a metal-organic framework (2). The metal-organic framework (2) had a water adsorption amount of 34.96 wt %.

Preparation Example 3

Preparation Example 3 was performed in the same manner as Preparation Example 1 except that the molar ratio of the 3,5-pyridinedicarboxylic acid to the aluminum nitrate was increased from 1:1 to 3:1, obtaining a metal-organic framework (3). The metal-organic framework (3) had a water adsorption amount of 33.81 wt %.

Preparation Example 4

Preparation Example 4 was performed in the same manner as Preparation Example 1 except that the molar ratio of the 3,5-pyridinedicarboxylic acid to the aluminum nitrate was increased from 1:1 to 4:1, obtaining a metal-organic framework (4). The metal-organic framework (4) had a water adsorption amount of 13.4 wt %.

Preparation Example 5

Preparation Example 5 was performed in the same manner as Preparation Example 1 except that the molar ratio of the 3,5-pyridinedicarboxylic acid to the aluminum nitrate was reduced from 1:1 to 1:2, obtaining a metal-organic framework (5). The metal-organic framework (5) had a water adsorption amount of 28.42 wt %.

Preparation Example 6

Preparation Example 6 was performed in the same manner as Preparation Example 1 except that the molar ratio of the 3,5-pyridinedicarboxylic acid to the aluminum nitrate was reduced from 1:1 to 1:3, obtaining a metal-organic framework (6). The metal-organic framework (6) had a water adsorption amount of 17.85 wt %.

Preparation Example 7

Preparation Example 7 was performed in the same manner as Preparation Example 1 except that the amount of water was increased from 72 mL to 87 mL and the amount of dimethylformamide was reduced from 18 mL to 3 mL, obtaining a metal-organic framework (7). The metal-organic framework (7) had a water adsorption amount of 34.90 wt %.

Preparation Example 8

Preparation Example 8 was performed in the same manner as Preparation Example 1 except that the amount of water was increased from 72 mL to 81 mL and the amount of dimethylformamide was reduced from 18 mL to 9 mL, obtaining a metal-organic framework (8). The metal-organic framework (8) had a water adsorption amount of 35.20 wt %.

Preparation Example 9

Preparation Example 9 was performed in the same manner as Preparation Example 1 except that the amount of water was increased from 72 mL to 76.5 mL and the amount of dimethylformamide was reduced from 18 mL to 13.5 mL, obtaining a metal-organic framework (9). The metal-organic framework (9) had a water adsorption amount of 34.30 wt %.

Preparation Example 10

Preparation Example 10 was performed in the same manner as Preparation Example 1 except that the amount of water was increased from 72 mL to 75 mL and the amount of dimethylformamide was reduced from 18 mL to 15 mL, obtaining a metal-organic framework (10). The metal-organic framework (10) had a water adsorption amount of 35.66 wt %.

Preparation Example 11

Preparation Example 11 was performed in the same manner as Preparation Example 1 except that the amount of water was reduced from 72 mL to 67.5 mL and the amount of dimethylformamide was increased from 18 mL to 22.5 mL, obtaining a metal-organic framework (11). The metal-organic framework (11) had a water adsorption amount of 34.99 wt %.

Preparation Example 12

Preparation Example 12 was performed in the same manner as Preparation Example 1 except that the amount of water was reduced from 72 mL to 54 mL and the amount of dimethylformamide was increased from 18 mL to 36 mL, obtaining a metal-organic framework (12). The metal-organic framework (12) had a water adsorption amount of 31.17 wt %.

Preparation Example 13

Preparation Example 13 was performed in the same manner as Preparation Example 1 except that the amount of water was reduced from 72 mL to 30 mL and the amount of dimethylformamide was increased from 18 mL to 60 mL, obtaining a metal-organic framework (13). The metal-organic framework (13) had a water adsorption amount of 29.61 wt %.

Preparation Example 14

Preparation Example 14 was performed in the same manner as Preparation Example 1 except that 72 mL of water and 18 mL of dimethylformamide were replaced with 90 mL of dimethylformamide, obtaining a metal-organic framework (14). The metal-organic framework (14) had a water adsorption amount of 20.94 wt %.

Preparation Example 15

Preparation Example 15 was performed in the same manner as Preparation Example 1 except that aluminum nitrate was replaced with aluminum sulfate (wherein the molar ratio of the 3,5-pyridinedicarboxylic acid to the aluminum sulfate was 2:1), obtaining a metal-organic framework (15). The metal-organic framework (15) had a water adsorption amount of 25.3 wt %.

Preparation Example 16

Preparation Example 16 was performed in the same manner as Preparation Example 1 except that aluminum nitrate was replaced with zirconyl chloride ($ZrOCl_2 \cdot 8H_2O$) (wherein the molar ratio of the 3,5-pyridinedicarboxylic acid to the zirconyl chloride was 1:1), obtaining a metal-organic framework (16).

Preparation Example 17

Preparation Example 17 was performed in the same manner as Preparation Example 1 except that aluminum nitrate was replaced with chromium nitrate ($Cr(NO_3)_3 \cdot 9H_2O$) (wherein the molar ratio of the 3,5-pyridinedicarboxylic acid to the chromium nitrate was 1:1), obtaining a metal-organic framework (17). The metal-organic framework (17) had a water adsorption amount of 22.05 wt %.

Comparative Example 1

Comparative Example 1 was performed in the same manner as Preparation Example 1 except that aluminum nitrate was replaced with ferric nitrate ($Fe(NO_3)_3 \cdot 9H_2O$) (wherein the molar ratio of the 3,5-pyridinedicarboxylic acid to the ferric nitrate was 1:1), obtaining a metal-organic framework (18). The metal-organic framework (18) had a water adsorption amount of 0.79 wt %.

Comparative Example 2

Comparative Example 2 was performed in the same manner as Preparation Example 1 except that aluminum nitrate was replaced with copper nitrate ($Cu(NO_3)_2 \cdot 3H_2O$) (wherein the molar ratio of the 3,5-pyridinedicarboxylic acid to the copper nitrate was 1:1), obtaining a metal-organic framework (19). The metal-organic framework (19) had a water adsorption amount of 0.66 wt %.

Comparative Example 3

Comparative Example 3 was performed in the same manner as Preparation Example 1 except that 3,5-pyridinedicarboxylic acid was replaced with 2,6-pyridinedicarboxylic acid (wherein the molar ratio of the 2,6-pyridinedicarboxylic acid to the aluminum nitrate was 1:1), obtaining a metal-organic framework (20). The metal-organic framework (20) had a water adsorption amount of 0 wt %.

Comparative Example 4

Comparative Example 4 was performed in the same manner as Preparation Example 1 except that 3,5-pyridinedicarboxylic acid was replaced with 2,4-pyridinedicarboxylic acid (wherein the molar ratio of the 2,4-pyridinedicarboxylic acid to the aluminum nitrate was 1:1), obtaining a metal-organic framework (21). The metal-organic framework (21) had a water adsorption amount of 9.8 wt %.

Comparative Example 5

First, aluminum nitrate (0.015 mole), 3,5-pyridinedicarboxylic acid (0.015 mole) and water (90 mL) were mixed, wherein the molar ratio of 3,5-pyridinedicarboxylic acid to the aluminum nitrate was 1:1. Next, the mixture was stirred at 120° C. for 48 hrs. Next, after cooling to room temperature, yellow sediment was collected. After washing the yellow sediment with water and filtering, a yellow solid was obtained. Next, the yellow solid was dried with a dryer (having a drying temperature of about 140° C.) overnight. After drying, the yellow solid was ground into powder. Next, the powder was subjected to a vacuum drying process in a vacuum drying oven, wherein the temperature of the vacuum drying process was about 140° C., and the vacuum drying process was performed for a period of 6 hrs. After cooling to room temperature, no metal-organic framework was obtained.

Table 1 shows the water adsorption amount of the metal-organic frameworks of Preparation Example 1 and Comparative Examples 1-5.

TABLE 1

| | water adsorption amount (wt %) |
|---|---|
| Preparation Example 1 | 34.48 |
| Comparative Example 1 | 0.79 |
| Comparative Example 2 | 0.66 |
| Comparative Example 3 | 0 |
| Comparative Example 4 | 9.8 |
| Comparative Example 5 | No metal-organic framework was obtained |

As shown in Table 1, the metal-organic frameworks of the disclosure exhibit a water adsorption amount of about 35 wt % when the metal-organic frameworks of the disclosure are prepared from specific ligands (such as 3,5-pyridinedicarboxylic acid) and a suitable metal ion. Conversely, the metal-organic frameworks (such as the metal-organic frameworks of Comparative Examples 3 and 4) prepared from ligands (such as 2,6-pyridinedicarboxylic acid or 2,4-pyridinedicarboxylic acid), having a similar structure as 3,5-pyridinedicarboxylic acid, exhibit a poor water adsorption amount. Furthermore, when preparing the metal-organic frameworks from an unsuitable metal ion (such as iron ion or copper ion) with specific ligands (such as 3,5-pyridinedicarboxylic acid), the obtained metal-organic frameworks (such as the metal-organic framework of Comparative Examples 1 and 2) exhibit a poor water adsorption amount (less than 1 wt %). In addition, as shown in Comparative Example 5, when the composition only employs water as solvent (i.e. the composition does not further include organic solvent, alkali metal hydroxide, and aluminate), no metal-organic framework can be obtained by subjecting the composition to a heating process.

Preparation Example 18

First, 3,5-pyridinedicarboxylic acid (9 mmole), sodium hydroxide (18 mmol), and water (15.78 mL) were mixed. Next, aluminum nitrate aqueous solution ($Al(NO_3)_3 \cdot 9H_2O$) (1M, 6.75 mmol) and sodium aluminate aqueous solution ($NaAlO_2$)(0.5M, 2.25 mmol) were added into the mixture, obtaining a composition after stirring. In particular, the molar ratio of the 3,5-pyridinedicarboxylic acid to aluminum nitrate was 4:3. The initial concentration of aluminum nitrate in the composition was 0.28 mol/L. The initial concentration of sodium aluminate in the composition was 0.09 mol/L. Next, the composition was stirred at 130° C. for 3 hrs. Next, after cooling to room temperature, a sediment was collected. After washing the sediment with water and filtering, a solid was obtained. Next, the solid was dried with a dryer (having a drying temperature of about 80° C.) overnight. After drying, the solid was ground into powder, obtaining a metal-organic framework (22). The metal-organic framework (22) had a water adsorption amount of 33.65 wt %.

Water served as solvent in Preparation Example 18 and Comparative Example 5, but composition of Preparation Example 18 for preparing the metal-organic framework further includes alkali metal hydroxide (i.e. sodium hydroxide). Therefore, the composition (aqueous solution) is at neutral pH and able to be dissolved with water. By contrast, the composition of Comparative Example 5 cannot not be used for preparing the metal-organic framework due to the absence of alkali metal hydroxide Preparation Example 19

Preparation Example 19 was performed in the same manner as Preparation Example 18 except in the absence of sodium aluminate aqueous solution, obtaining a metal-organic framework (23). The metal-organic framework (23) had a water adsorption amount of 25.43 wt %.

Preparation Example 20

Preparation Example 20 was performed in the same manner as Preparation Example 18 except that the initial concentration of sodium aluminate aqueous solution was reduced from 0.09 mol/L to 0.05 mol/L, obtaining a metal-organic framework (24). The metal-organic framework (24) had a water adsorption amount of 32.13 wt %.

Preparation Example 21

Preparation Example 21 was performed in the same manner as Preparation Example 18 except that the initial concentration of sodium aluminate aqueous solution was reduced from 0.09 mol/L to 0.07 mol/L, obtaining a metal-organic framework (25). The metal-organic framework (25) had a water adsorption amount of 31.80 wt %.

Preparation Example 22

Preparation Example 22 was performed in the same manner as Preparation Example 18 except that the initial concentration of sodium aluminate aqueous solution was increased from 0.09 mol/L to 0.11 mol/L, obtaining a metal-organic framework (26). The metal-organic framework (26) had a water adsorption amount of 33.47 wt %.

Preparation Example 23

Preparation Example 23 was performed in the same manner as Preparation Example 18 except that the initial concentration of sodium aluminate aqueous solution was increased from 0.09 mol/L to 0.15 mol/L, obtaining a metal-organic framework (27). The metal-organic framework (27) had a water adsorption amount of 27.77 wt %.

Table 2 shows the water adsorption amount of the metal-organic frameworks of Examples 18-23.

TABLE 2

| | initial concentration of sodium aluminate aqueous solution (mol/L) | water adsorption amount (wt %) |
|---|---|---|
| Preparation Example 18 | 0.09 | 33.65 |
| Preparation Example 19 | 0 | 25.43 |
| Preparation Example 20 | 0.05 | 32.13 |
| Preparation Example 21 | 0.07 | 31.80 |
| Preparation Example 22 | 0.11 | 33.47 |
| Preparation Example 23 | 0.15 | 27.77 |

As shown in Table 2, in comparison with the composition in the absence of sodium aluminate, the addition of sodium aluminate (with an initial concentration of sodium aluminate aqueous solution between 0.05 mol/L and 0.15 mol/L) can enhance the water adsorption amount of the obtained metal-organic framework when the solvent of the composition is water. The reason is that sodium aluminate in the composition can serve as an inhibitor, which inhibits the formation of crystalline by-products when reacting 3,5-pyridinedicarboxylic acid with the metal compound.

Preparation Example 24

Preparation Example 24 was performed in the same manner as Preparation Example 18 except that the reaction temperature of the composition was reduced from 130° C. to 110° C., obtaining a metal-organic framework (28). The metal-organic framework (28) had a water adsorption amount of 32.17 wt %.

Preparation Example 25

Preparation Example 25 was performed in the same manner as Preparation Example 18 except that the reaction temperature of the composition was reduced from 130° C. to 120° C., obtaining a metal-organic framework (29). The metal-organic framework (29) had a water adsorption amount of 32.67 wt %.

As shown in Preparation Examples 18, 24 and 25, the reaction temperature of the composition may be between 110° C. to 130° C., when the solvent of the composition for preparing the metal-organic framework is water.

Preparation Example 26

Preparation Example 26 was performed in the same manner as Preparation Example 18 except that the reaction time period was reduced from 3 hrs to 2 hrs, obtaining a metal-organic framework (30). The metal-organic framework (30) had a water adsorption amount of 32.31 wt %.

As shown in Preparation Examples 18 and 26, the reaction time period may be between 2 hrs and 3 hrs, when the solvent of the composition for preparing the metal-organic framework is water.

Preparation Example 27

Preparation Example 27 was performed in the same manner as Preparation Example 18 except that the aluminum nitrate aqueous solution was replaced with zirconyl chloride ($ZrOCl_2 \cdot 8H_2O$) aqueous solution, obtaining a metal-organic framework (31).

Preparation Example 28

Preparation Example 28 was performed in the same manner as Preparation Example 18 except that the aluminum nitrate aqueous solution was replaced with chromium nitrate ($Cr(NO_3)_3 \cdot 9H_2O$) aqueous solution, obtaining a metal-organic framework (32).

Preparation Example 29

Preparation Example 29 was performed in the same manner as Preparation Example 18 except that the aluminum nitrate aqueous solution was replaced with aluminum sulfate ($Al_2(SO_4)_3 \cdot 14H_2O$) aqueous solution, obtaining a metal-organic framework (33). The metal-organic framework (33) had a water adsorption amount of 30.85 wt %.

Preparation Example 30

Preparation Example 30 was performed in the same manner as Preparation Example 18 except that the aluminum nitrate aqueous solution was replaced with aluminum chloride ($AlCl_3 \cdot 6H_2O$) aqueous solution, obtaining a metal-organic framework (34). The metal-organic framework (34) had a water adsorption amount of 33.25 wt %.

Preparation Example 31

Preparation Example 31 was performed in the same manner as Preparation Example 18 except that the molar ratio of 3,5-pyridinedicarboxylic acid to aluminum nitrate was changed from 4:3 to 2:1, obtaining a metal-organic framework (35). The metal-organic framework (35) had a water adsorption amount of 31.86 wt %.

Preparation Example 32

Preparation Example 32 was performed in the same manner as Preparation Example 18 except that the molar ratio of 3,5-pyridinedicarboxylic acid to aluminum nitrate was changed from 4:3 to 1:1, obtaining a metal-organic framework (36). The metal-organic framework (36) had a water adsorption amount of 30.68 wt %.

Preparation Example 33

Preparation Example 33 was performed in the same manner as Preparation Example 18 except that the molar ratio of 3,5-pyridinedicarboxylic acid to aluminum nitrate was changed from 4:3 to 1:2, obtaining a metal-organic framework (37). The metal-organic framework (37) had a water adsorption amount of 30.67 wt %.

Preparation Example 34

Preparation Example 34 was performed in the same manner as Preparation Example 18 except that the initial concentration of aluminum nitrate in the composition was reduced from 0.28 mol/L to 0.22 mol/L, obtaining a metal-organic framework (38). The metal-organic framework (38) had a water adsorption amount of 31.86 wt %.

Preparation Example 35

Preparation Example 35 was performed in the same manner as Preparation Example 18 except that the initial concentration of aluminum nitrate in the composition was increased from 0.28 mol/L to 0.33 mol/L, obtaining a metal-organic framework (39). The metal-organic framework (39) had a water adsorption amount of 30.68 wt %.

Preparation Example 36

Preparation Example 36 was performed in the same manner as Preparation Example 18 except that the initial concentration of aluminum nitrate in the composition was increased from 0.28 mol/L to 0.56 mol/L, obtaining a metal-organic framework (40). The metal-organic framework (40) had a water adsorption amount of 30.67 wt %.

Preparation Example 37

Preparation Example 37 was performed in the same manner as Preparation Example 18 except that the initial concentration of aluminum nitrate in the composition was increased from 0.28 mol/L to 0.66 mol/L, obtaining a metal-organic framework (41). The metal-organic framework (41) had a water adsorption amount of 30.24 wt %.

As shown in Preparation Examples 18, 34 and 37, the initial concentration of aluminum nitrate in the composition may be between 0.22 mol/L and 0.66 mol/L, when the solvent of the composition for preparing the metal-organic framework is water.

Preparation Example 38

Preparation Example 38 was performed in the same manner as Preparation Example 18 except that 3 mL of ethanol was added into the composition, obtaining a metal-organic framework (42). The metal-organic framework (42) had a water adsorption amount of 32.71 wt %.

Preparation Example 39

Preparation Example 39 was performed in the same manner as Preparation Example 18 except that 6 mL of ethanol was added into the composition, obtaining a metal-organic framework (43). The metal-organic framework (43) had a water adsorption amount of 33.92 wt %.

Preparation Example 40

Preparation Example 40 was performed in the same manner as Preparation Example 18 except that 9 mL of ethanol was added into the composition, obtaining a metal-organic framework (44). The metal-organic framework (44) had a water adsorption amount of 33.88 wt %.

Table 3 shows the water adsorption amount of the metal-organic framework disclosed in Preparation Examples 18, 38 and 40.

TABLE 3

| | ethanol (mL) | water adsorption amount (wt %) |
|---|---|---|
| Preparation Example 18 | 0 | 33.65 |
| Preparation Example 38 | 3 | 32.71 |
| Preparation Example 39 | 6 | 33.92 |
| Preparation Example 40 | 9 | 33.88 |

As shown in Table 3, the water adsorption amounts of metal-organic frameworks are similar regardless of the presence/absence of the addition of ethanol, when the solvent of the composition for preparing the metal-organic framework is water.

Thermogravimetric Analysis (TGA) Curves of Metal-Organic Framework

Example 1

Thermogravimetric Analysis (TGA) Curves of Metal-Organic Framework

Figure 1:
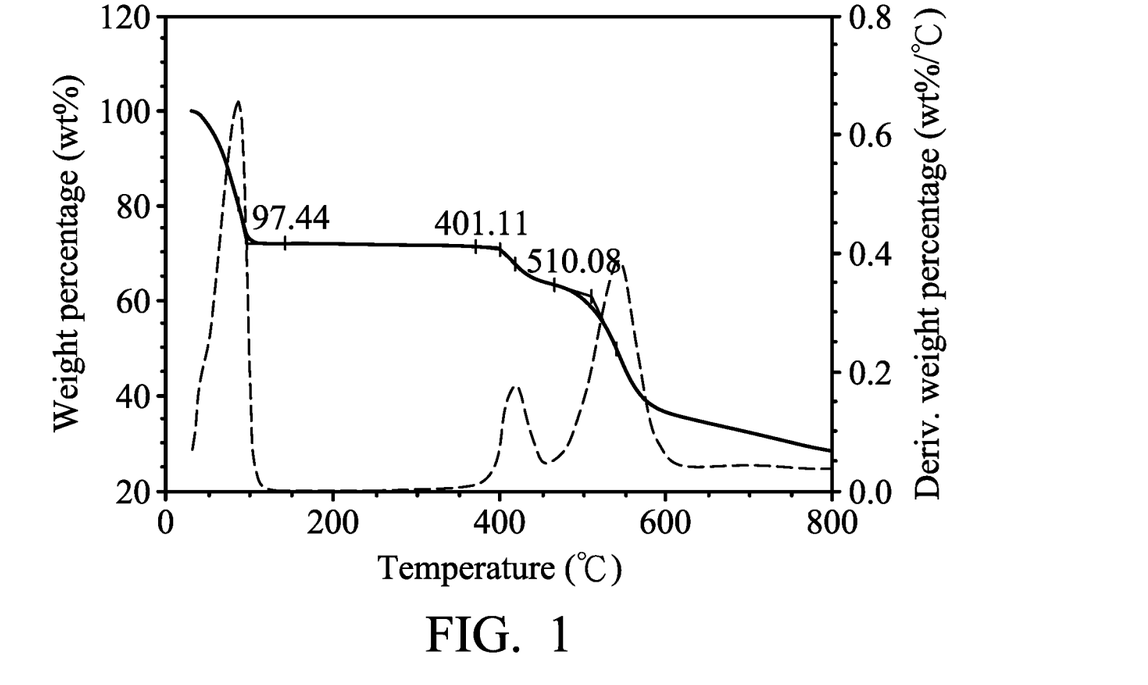
FIG. 1 shows the thermogravimetric analysis (TGA) curves of the metal-organic framework of Preparation Example 1.

The amount of water desorption and desorption temperature of the metal-organic framework (1) of Preparation Example 1 were determined by thermogravimetric analysis (TGA), and the result is shown in FIG. 1.

The weight loss of the metal-organic framework (1) of Preparation Example 1 (disposed in a thermogravimetric analyzer) was recorded with a heating rate of 10° C./min. As shown in FIG. 1, the weight of the metal-organic framework (1) of Preparation Example 1 was significantly reduced from 50° C. to 100° C. The metal-organic framework (1) had a weight loss of about 30% at 100° C. This means that the metal-organic framework can adsorb water and the water adsorbed by the metal-organic framework can be desorbed at low temperature (about 50° C.). As shown in FIG. 1, the metal-organic framework (1) had a weight loss again until the temperature was raised to about 400° C. This means that the metal-organic framework of the disclosure exhibits high thermal stability (more than 400° C.).

Isothermal Adsorption Analysis of Metal-Organic Framework

Example 2

Figure 2:
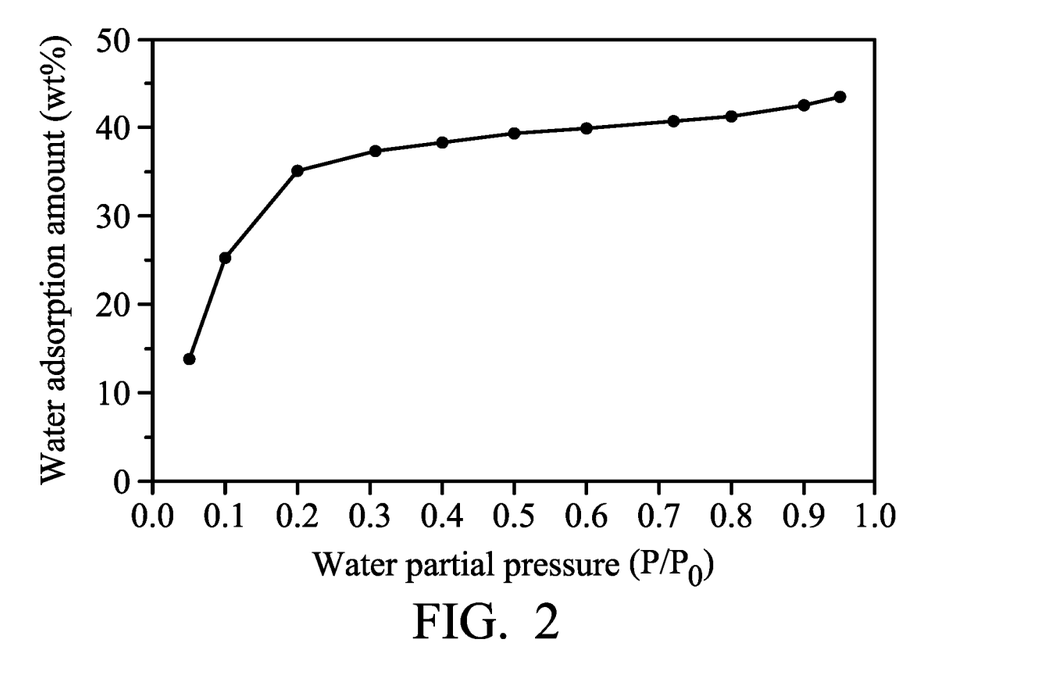
FIG. 2 shows the isothermal adsorption curve of the metal-organic framework of Preparation Example 1.

FIG. 2 shows the isothermal adsorption curve of the metal-organic framework of Preparation Example 1. First, the metal-organic framework of Preparation Example 1 was heated at 80° C. to desorb water under vacuum. Next, the partial pressure of water was gradually increased at 25° C. under vacuum. In detail, 0.1 partial pressure of water was introduced each time. As a result, the metal-organic framework gradually adsorbed water, and then the water adsorption amount of the metal-organic framework was determined at a specific partial pressure of water. As shown in FIG. 2, when the partial pressure of water was increased to 0.2, the water adsorption amount of the metal-organic framework was significantly increased to 35 wt %. The water adsorption amount of the metal-organic framework is increased to 40% with the slow increase of partial pressure of water. This means that the metal-organic framework of the disclosure exhibits a high water adsorption amount under a low relative humidity.

Adsorption Test Under a Low Relative Humidity

Example 3

Figure 3:
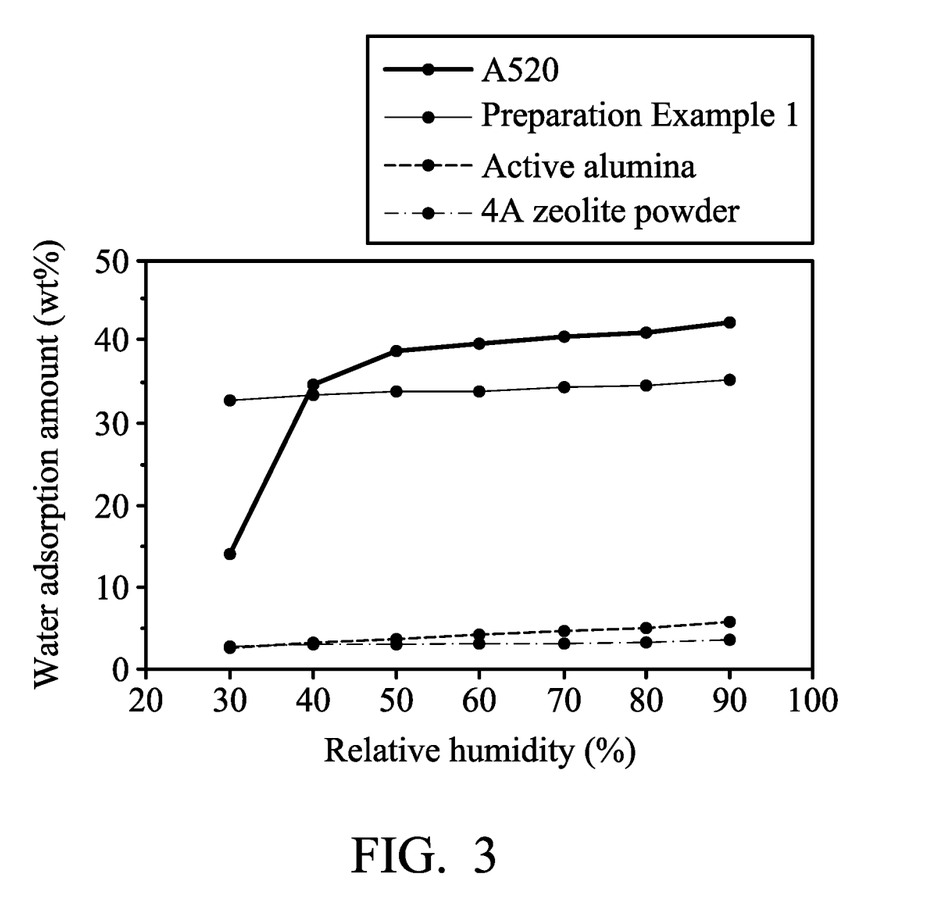
FIG. 3 is a graph plotting the water adsorption amount of the metal-organic framework of Preparation Example 1. Basolite® A520, active alumina and zeolite 4A powder against various relative humidity levels.

The water adsorption amount of the samples (including the metal-organic framework (1) of Preparation Example 1, an adsorption material (commercially available under the trade name Basolite® A520), an active alumina (commercially available from Eikme International LTD) and zeolite 4A powder (commercially available from Eikme International LTD)) were determined by an adsorption test under a low relative humidity. First, the samples were dried to desorb water at 80° C. for 30 minutes, and then disposed in a constant temperature and humidity chamber at 25° C. under a relative humidity of 30%. After 30 minutes, the water adsorption amounts of the samples were determined. Next, the relative humidity of the constant temperature and humidity chamber was increased to 40%, and then the water adsorption amounts of the samples were determined again after 30 minutes. The above steps are repeated until the relative humidity of the chamber was increased to 90%. The results are shown in FIG. 3. As shown in FIG. 3, the water adsorption amount of the metal-organic framework (1) of Preparation Example 1 can be 33 wt % after disposing the metal-organic framework (1) of Preparation Example 1 in the humidistat under a relative humidity of 30% for 30 minutes. In contrast, the adsorption material (commercially available under the trade name Basolite® A520) had a water adsorption amount of 14 wt % after disposing in the chamber under a relative humidity of 30% for 30 minutes. Therefore, the adsorption material (commercially available under the trade name Basolite® A520) does not exhibit a rapid water adsorption property under a low relative humidity during the same time period. As shown in FIG. 3, the active alumina (conditional adsorption material) and the zeolite 4A powder were dried at 80° C. for 30 minutes to desorb water. Due to the small pore size of the active alumina and the zeolite 4A powder, water adsorbed by the active alumina and the zeolite 4A powder cannot be removed completely at a low temperature (80° C.), resulting in the pores of active alumina and the zeolite 4A powder still filling with water. As a result, the water adsorption amount of the active alumina and the zeolite 4A powder are both less than 6 wt % even though the active alumina and the zeolite 4A powder are disposed in the humidistat under a relative humidity of 90%. This means that those conditional adsorption materials exhibit a poor water adsorption capacity under a low relative humidity.

Example 4

Figure 4:
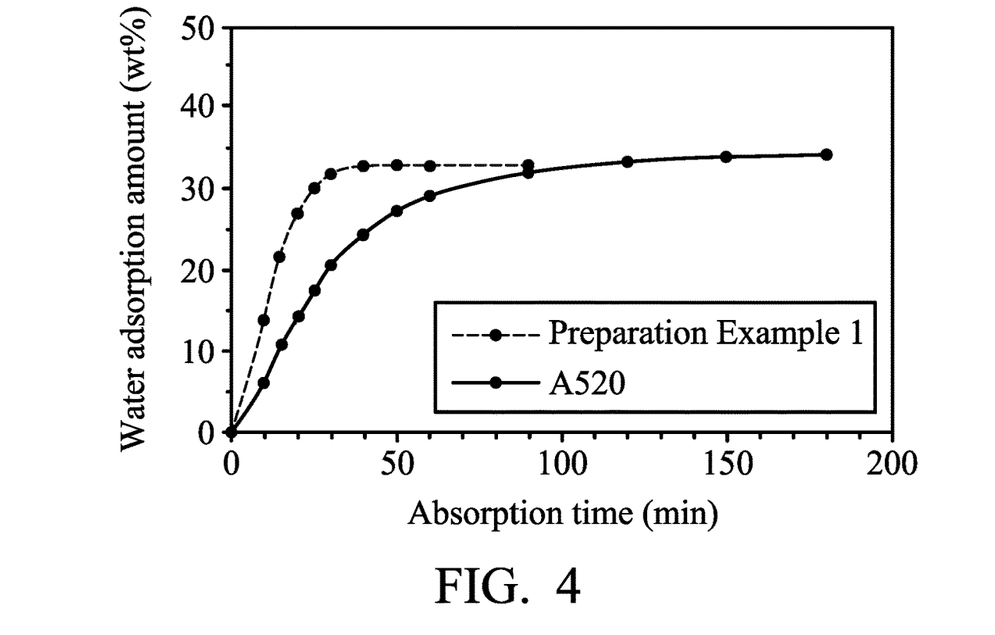
FIG. 4 is a graph plotting the water adsorption amount of the metal-organic framework of Preparation Example 1 and Basolite® A520 (under a relative humidity of 30%) against time.

The water adsorption capacity of the metal-organic framework (1) of Preparation Example 1 were compared with that of the adsorption material (commercially available under the trade name Basolite® A520) under a low relative humidity. First, the metal-organic framework (1) of Preparation Example 1 and the adsorption material (commercially available under the trade name Basolite® A520) were dried at 80° C. for 30 minutes. Next, the water adsorption amount of the metal-organic framework (1) of Preparation Example 1 and the adsorption material (commercially available under the trade name Basolite® A520) were determined after disposing these samples in a Constant temperature and humidity chamber at 25° C. under a relative humidity of 30%. As shown in FIG. 4 and Table 4, the metal-organic framework (1) of Preparation Example 1 exhibits a water adsorption amount greater than 30 wt % at 25 minutes. In contrast, the adsorption material (commercially available under the trade name Basolite® A520) exhibits a water adsorption amount about 30 wt % after 60 minutes. This means that the metal-organic framework (1) of Preparation Example 1 can exhibit a rapid water adsorption property under a low relative humidity.

TABLE 4

|  | Preparation Example 1 | Adsorption material (commercially available under the tradename Basolite ® A520) |
| --- | --- | --- |
| Time required for achieving the water adsorption amount of 30 wt % | 25 minutes | 60 minutes |

Example 5

Figure 5:
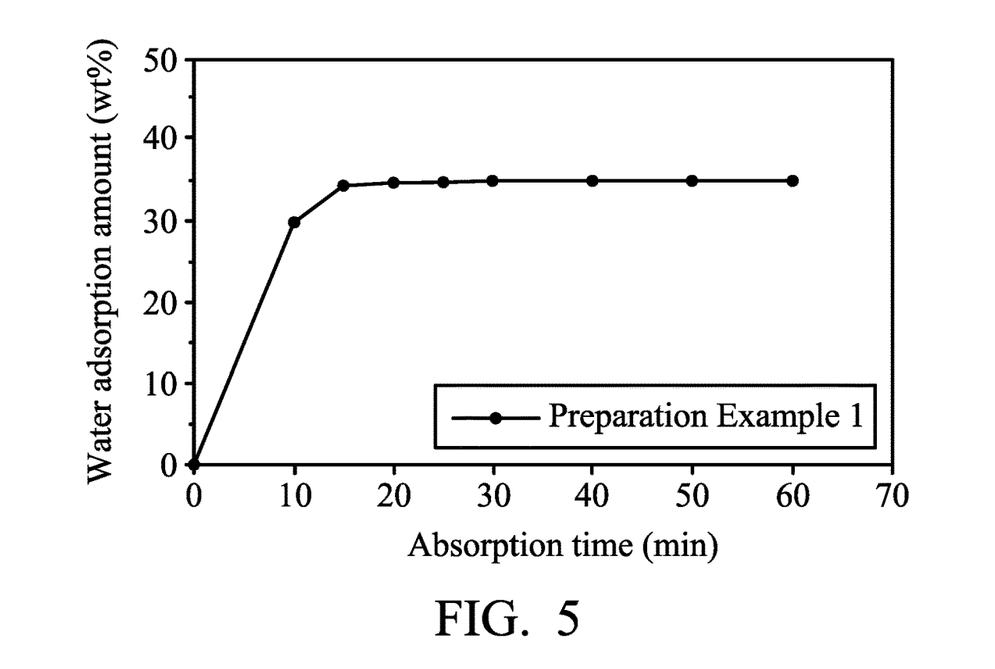
FIG. 5 is a graph plotting the water adsorption amount of the metal-organic framework of Preparation Example 1 (under a relative humidity of 80%) against time.

Example 5 was performed in the same manner as Example 4 except that the relative humidity of the constant temperature and humidity chamber was increased from 30% to 80%, and the result is shown in FIG. 5. As shown in FIG. 5, the metal-organic framework (1) of Preparation Example 1 exhibits a water adsorption amount greater than 30 wt % after 10 minutes and exhibits a water adsorption amount of 34 wt % at 30 minutes. This means that the metal-organic framework (I) of Preparation Example 1 can exhibit a high water adsorption capacity under a high relative humidity.

Example 6

The metal-organic frameworks of Comparative Examples 1, 3 and 4 were dried at 80° C. for 30 minutes. Next, those samples were disposed in a constant temperature and humidity chamber at 25° C. under a relative humidity of 30%. After 30 minutes, the water adsorption amounts of those samples were determined and the results are shown in Table 5. Next, those samples were disposed in the chamber at 25° C. under a relative humidity of 80%. After 30 minutes, the water adsorption amounts of those samples were determined and the results are shown in Table 5.

TABLE 5

|  | Preparation Example 1 | Comparative Example 1 | Comparative Example 3 | Comparative Example 4 |
| --- | --- | --- | --- | --- |
| RH 80% for 30 minutes | 34 wt % | 5.43 wt % | 0 | 9.8 wt % |
| RH 30% for 30 minutes | 33 wt % | 0.79 wt % | 0 | 6.08 wt % |

As shown in Table 5, the water adsorption amount of the metal-organic framework of Preparation Example 1 is 34 wt % under a relative humidity of 80%. In comparison with Comparative Examples, the water adsorption amount of the metal-organic framework of Preparation Example 1 exhibits a high water adsorption capacity.

Furthermore, the metal-organic framework of the disclosure also exhibits a water adsorption amount of 33 wt % even though the metal-organic framework is used under a low relative humidity (such as 30%).

In view of the examples, the metal-organic framework of the disclosure exhibits high water adsorption amount (greater than 30 wt %) under low and high relative humidity. In addition, water adsorbed by conventional adsorption materials (such as zeolite 4A and active alumina) would be desorbed therefrom at a relative high temperature (about 100° C.). In contrast, water adsorbed by the metal-organic framework of the disclosure can be desorbed therefrom at a relative low temperature (about 80° C.) to regenerate the water adsorption capacity. As a result, the metal-organic framework of the disclosure can adsorb water at low relative humidity and desorb water at low temperatures.

It will be clear that various modifications and variations can be made to the disclosed methods and materials. It is intended that the specification and examples be considered as exemplary only, with the true scope of the disclosure being indicated by the following claims and their equivalents.

What is claimed is:

1. A method for preparing a metal-organic framework, comprising:
   providing a composition, wherein the composition comprises a 3,5-pyridinedicarboxylic acid, a metal compound, an alkali metal hydroxide, and a solvent, wherein the solvent is water; and
   subjecting the composition to a heating process so that the 3,5-pyridinedicarboxylic acid reacts with the metal compound, obtaining a metal-organic framework.

2. The method as claimed in claim 1, wherein the molar ratio of 3,5-pyridinedicarboxylic acid to the metal compound is from 3:1 to 1:2.

3. The method as claimed in claim 1, wherein the metal compound is aluminum salt, chromium salt, zirconium salt, or a combination thereof.

4. The method as claimed in claim 1, wherein the metal compound is aluminum nitrate, aluminum sulfate, aluminum chloride, aluminum phosphate, chromium nitrate, chromium phosphate, zirconium nitrate, zirconium phosphate, zirconyl chloride, or a combination thereof.

5. The method as claimed in claim 1, wherein an initial concentration of the metal compound in the composition is from 0.15 mol/L to 0.66 mol/L.

6. The method as claimed in claim 1, wherein the alkali metal hydroxide comprises lithium hydroxide, sodium hydroxide, potassium hydroxide, or a combination thereof.

7. The method as claimed in claim 1, wherein the molar ratio of the alkali metal hydroxide to 3,5-pyridinedicarboxylic acid is between 1.8 and 2.2.

8. The method as claimed in claim 1, wherein the composition further comprises an aluminate.

9. The method as claimed in claim 8, wherein the aluminate comprises lithium aluminate, sodium aluminate, potassium aluminate, magnesium aluminate, calcium aluminate, or a combination thereof.

10. The method as claimed in claim 8, wherein an initial concentration of the aluminate in the composition is between 0.05 mol/L and 0.20 mol/L.

11. The method as claimed in claim 1, wherein the heating process has a temperature from 100° C. to 150° C.

12. The method as claimed in claim 1, wherein the heating process is performed for a period of 1 hr to 66 hrs.

* * * * *